United States Patent
Gonzáles de la Rosa

[11] Patent Number: 5,864,385
[45] Date of Patent: Jan. 26, 1999

[54] METHOD OF DETERMINING THE PERIMETER OF THE VISUAL FIELD OF THE HUMAN EYE

[76] Inventor: Manuel Gonzáles de la Rosa, 25 de Julio, 34, 38004 Santa Cruz de Tenerife Islas Canarias, Spain

[21] Appl. No.: 703,334

[22] Filed: Aug. 26, 1996

[30] Foreign Application Priority Data

Sep. 20, 1995 [CH] Switzerland .............................. 2652/95
Dec. 8, 1995 [CH] Switzerland .............................. 3468/95

[51] Int. Cl.⁶ ....................................................... A61B 3/00
[52] U.S. Cl. ............................................. 351/246; 351/224
[58] Field of Search ..................................... 351/200, 222, 351/224, 237, 226, 246

[56] References Cited

U.S. PATENT DOCUMENTS 5,412,561 5/1995 Rosenshein et al. .................... 351/224

FOREIGN PATENT DOCUMENTS 0495247 7/1992 European Pat. Off. .

Primary Examiner—Huy Mai
Attorney, Agent, or Firm—Martin A. Farber

[57] ABSTRACT

A multiplicity of test sites determined by coordinates are stipulated in the visual field. This is done in such a way that at least one further test site is present within a specific circle around each test site and a stimulus is applied only once at each test site. A value for the stimulus is stipulated and recorded for each test site. The first stimulus of a series of stimuli forming an examination is applied at any desired test site using the stimulus. For this test site and the test sites located within its circle, the stimulus value is corrected according to a mathematical function corresponding to the patient response towards the threshold value, and these are recorded as corrected stimuli. The second stimulus and the following stimuli which are applied at the other test sites in any desired sequence have the stimulus value or the corrected stimulus value recorded for the respective test site.

7 Claims, 4 Drawing Sheets

METHOD OF DETERMINING THE PERIMETER OF THE VISUAL FIELD OF THE HUMAN EYE

FIELD AND BACKGROUND OF THE INVENTION

The present invention relates to a method of determining the perimeter of the visual field of the human eye.

The visual field of the human eye is determined by the retinal light-sensitivity. The light-sensitivity values within the visual field are determined by means of a perimeter. For this purpose, various methods are known, in all of which a number of test sites within the visual field are examined and for which the threshold value of perception is determined. Computer-controlled perimeters are suitable, which are programmed in accordance with the method of determination.

It is known to determine the retinal light-sensitivity at the specific test sites stipulated by coordinates by applying light stimuli of different intensity (brightness or magnitude) using a perimeter. The subjects respond during an examination by pressing a response button when the light stimulus is perceived. If the light stimulus is not seen, the response button is not pressed. During this procedure, the light stimuli are applied in a graduated manner with greater and lesser intensity in such way that the sensitivity threshold is exceeded one or more times. After the sensitivity threshold has been exceeded, the direction of alteration of the stimulus intensity changes in each case from brighter to darker or vice versa. At the same time, the magnitude of the alteration is reduced (e.g. to half the previous value) until the sensitivity threshold has been bracketed, that is to say the threshold value of perception has been determined.

By definition, the threshold value of perception (retinal sensitivity in decibels) corresponds to that stimulus intensity (in apostilb) of which, after a specific number of applications, half were seen and half were not seen. The retinal sensitivity is expressed as a logarithmic function of the quotient calculated from the maximum stimulus intensity divided by the stimulus intensity applied. The formula for retinal sensitivity is:

$$\text{Ret. sensitivity (dB)} = {}^{10}\log \frac{\text{max. stimulus intensity}}{\text{stimulus intensity applied}}$$

This means that the retinal sensitivity is identified as 0 dB if the brightest stimulus (e.g. 1,000 or 10,000 asb) is not seen. High stimulus intensities correspond to low sensitivity values.

According to this known method, determining the retinal sensitivity by bracketing requires four to six stimulus applications per test site. Since the retinal sensitivity of the visual field is usually determined by measurements at 50 to 100 test sites, between 200 and 600 stimulus applications are required for each examination of the visual field. Such an examination therefore usually lasts between 7 and 20 minutes. For reasons of efficiency, due to accuracy problems caused by the progressive slowing-down of retinal renewal (fatigue) and due to insufficient reliability through incorrect responses with diminishing concentration of the subjects, this duration of the examination is considered to be too long.

SUMMARY OF THE INVENTION

The present invention is therefore based on the objective of specifying a method and an apparatus with which the threshold values of the retinal sensitivity of a visual field can be determined within a far shorter time.

The invention reliably achieves this objective because it takes into account biological dependencies and interrelations. Adjacent sites within the visual field are anatomically connected both by the retinal cellular interrelations and by the structure of the optic tract to the occipital cortex. These relationships are known and result in most sensitivity losses affecting relatively large areas of the retina. Due to these interrelations, merely a single light stimulus is sufficient per test site, even in the case of a comparatively large interval between the test sites. Deep and sharply bounded defects are less common and generally correspond to the central area or the foveae of the retina.

BRIEF DESCRIPTION OF THE DRAWINGS

With the above-and other objects in view, the present invention will become more clearly understood in connection with the detailed description of a preferred embodiment, when considered with the accompanying drawings of which:

FIG. 1 shows diagrammatically an array of grid points identifying test sites at which stimuli are to be located;

FIG. 2 shows a numbering of grid points identifying successive sequences of tests using different sets of grid points;

FIG. 3 shows retinal sensitivity of a standardized population sample of the same age as a person being tested;

FIG. 4 shows initial values of stimuli for a first test run;

FIG. 5 shows corrections of stimuli values for a test run;

FIG. 6 outlines locations of corrections to values of stimuli for a test run;

FIG. 7 shows values of stimuli for a second test run; and

DETAILED DESCRIPTION OF THE PREFERRED EMBODIMENT

Figures 1, 2:
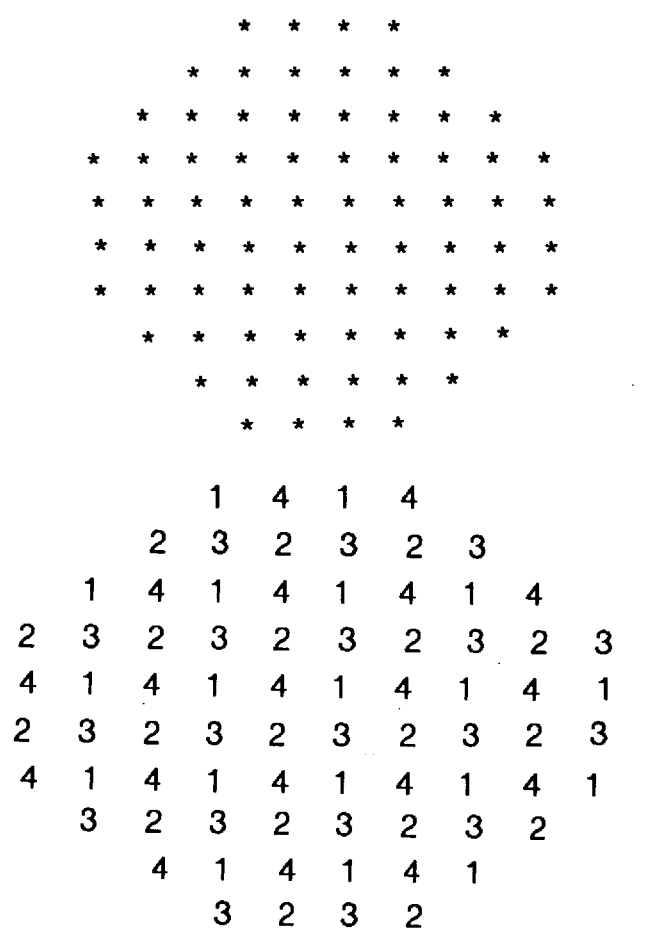
Figure 8:
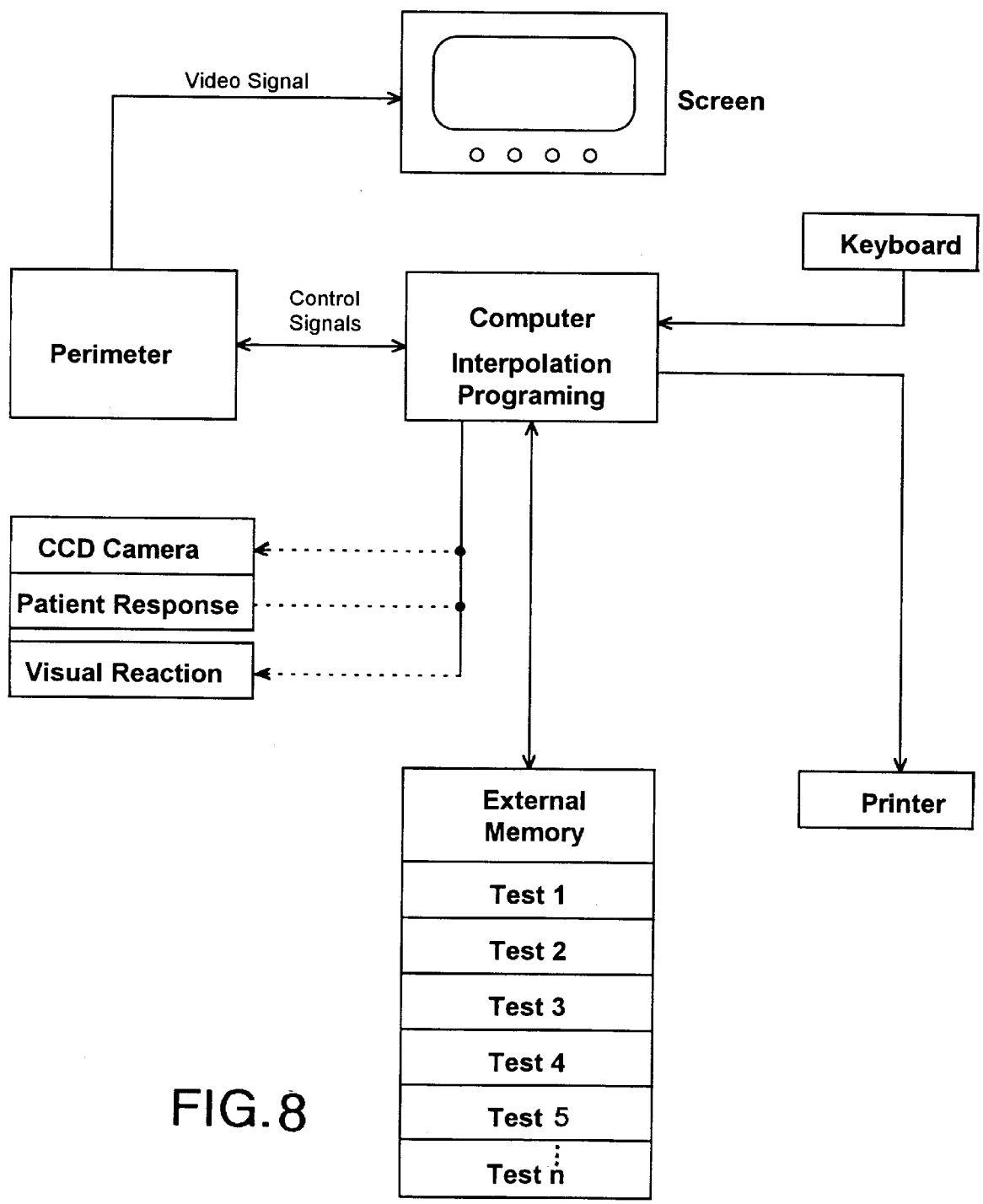
FIG. 8 shows apparatus, including a computer programmed with methodology of the invention, for practicing the invention.

The invention is to examine and determine the retinal sensitivity or the threshold value of perception in the 30° sector of the visual field of a subject, 76 regularly distributed test sites being stipulated by coordinates in this sector in a linear arrangement with a 6° division (FIG. 1). All the test sites (of this sector) are divided into four groups—denoted by the numerals 1 to 4 (FIG. 2). They can also be divided into fewer or more than four groups. These groups are examined one after another. In the case of all four groups 1 to 4, the mutual interval between the associated test sites is equal both in the X-direction and in the Y-direction, such that test sites of two groups alternate regularly in each row. The test sites of the different groups 1 to 4 are thus distributed homogeneously within the area of the visual field.

The examination begins at any selected test site of group 1. The initial value of the stimulus intensity for the test sites of the first group 1 is preferably half the age-corrected standard value of the subject applicable for a test site (FIG. 4). These initial values are between 0 db (blind) and the retinal sensitivity of the standard-sighted population of the same age (FIG. 3). Other, e.g. sickness-dependent, initial values may likewise be used.

Each test site in each group 1 to 4 is examined only once, that is to say has a stimulus applied. The sequence of the test sites during the examination is selected at random.

Depending on the patient response (positive or negative) given at a test site to an applied stimulus, a predetermined value with a positive or negative sign, called a constant, is added to the stimulus of this test site in order to raise the stimulus given for this test site in the case of a YES response or to reduce it the case of a NO response.

The constant for the first group is greater than that of the second, and the constant of the second group is greater than that of the third group, etc. The constants are graded from the first to the last group approximately regularly towards lower values. If the constant "a" for the first group is taken to be ¼ of the age-corrected standard value, rounded to the nearest whole even number, that is to say 8 decibels, the following constants result, for example, for the four groups:

1st group, constant a 8 dB

2nd group, constant b 5 dB

3rd group, constant c 4 dB

4th group, constant d 2 dB.

Figures 5, 6, 7:
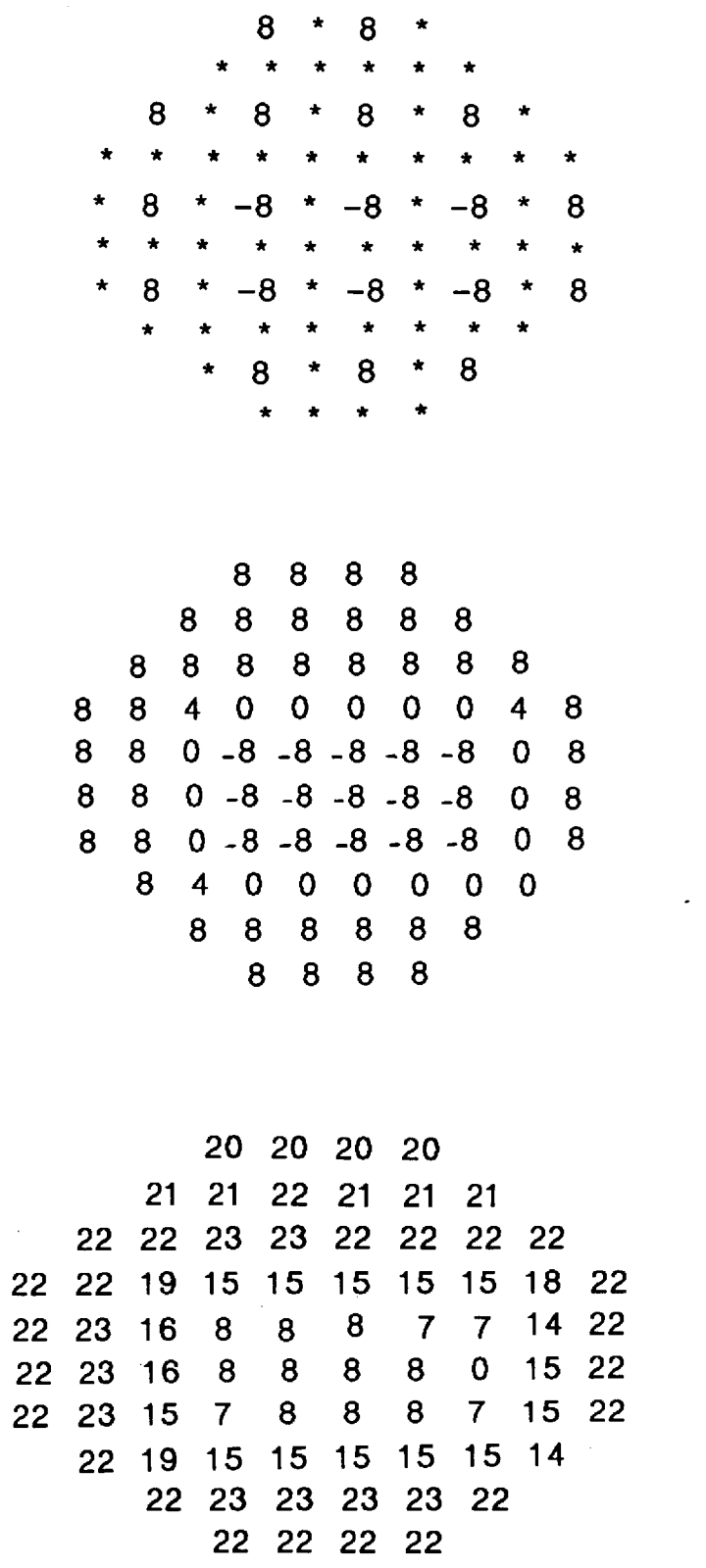

After the examination of the test sites of the first group, their stimulus are corrected by the group constant "a" (=8) in accordance with the subject responses with a positive or negative sign (FIG. 5). For the test sites of the other groups 2 to 4 located between the test sites of the first group, the stimuli are adapted by interpolation to the corrected stimulus of the first group 1. The corrections to be carried out in the process at the individual test sites are specified in FIG. 6.

These correction values (constants "a" and interpolated correction values) are added to or deducted from the previous stimulus values, that is to say the half, age-corrected standard values (depending on the sign of the correction value) and the new stimulus values applicable for the examination of the test sites of the second group 2 are thus stipulated (FIG. 7). The test sites of the second group 2 than have stimuli applied in accordance with the new stimulus values in any desired sequence. After the examination of the second group 2, depending on the patient (seen or not seen), a second constant "b" in the order of 6 dB with a positive or negative sign is added to the stimulus value of each test site of the second group, which has already been corrected once, and the corrected stimulus value is corrected again. The stimulus values of the test sites of the groups 1, 3 and 4 located between the test sites of the second group, these stimuli likewise already having been corrected once, are adapted, as was the case after the examination of the first group, by interpolation to the twice-corrected stimuli of the test sites of the second group 2, whereupon—following the same procedure—the sites of the groups 3 and 4 are examined and their corrected stimuli are newly stipulated taking into account the patient responses and the constants "c" and "d" and are approximated to the retinal light-sensitivity threshold. The corrected stimuli present after the examination of the test sites of the last group 4 thus constitute the sought threshold values of perception or of retinal sensitivity.

In the example of the method described, the test sites in the area of the visual field under examination are divided into groups, the test sites of the groups being distributed evenly over the examination area. Firstly, the test sites of the first group are examined in one step of the method, those of the second group are examined in a second step of the method, etc. Each test site is assigned a value for the stimulus to be applied there. At the test sites examined during one step of the method, the stimuli are increased or decreased by a constant value in accordance with the patient response (seen or not seen). The stimuli for the test sites not examined during one step of the method are adapted, in each case by interpolation or extrapolation, to the stimuli corrected in this step of the method.

The constant value used to correct the stimulus values of the test sites examined in each case during one step of the method becomes smaller from one step of the method to another. The constant value of the last step of the method preferably corresponds to the smallest difference between two stimuli, which is necessary to calculate the threshold value in the bracketing method, that is to say two decibels.

The stimulus brightness is the intensity of the light stimulus applied to the subject. The greatest intensity (in apostilb) is required wherever the visual field of the subject is reduced. The smallest intensities are applied at test sites with standard sensitivity.

The so-called standard values which are important for stipulating the stimuli value are recorded for each perimeter model in clinical trials. They also form the basis for determining defects in retinal sensitivity. The standard values are age-dependent and are determined for various age groups.

Although, in the example described, the test sites within the groups 1 to 4 are in linear arrangement, a non-linear arrangement may also be selected. It is likewise possible to select a different division from 6°.

A perimeter such as is described, for example, in EP-A-495 247 is suitable for carrying out the method, in which case the computer is programmed or must be programmable in accordance with the method, and the stimulus values must be contained in the internal or external memory.

I claim:

1. Method for testing visual function of the human eye, comprising steps of:

selecting a multiplicity of test sites determined by coordinates being stipulated in a visual field, that at least one further test site is present within a predetermined circle around each test site;

applying a stimulus only once at each test site, an initial value for the stimulus being stipulated and recorded for each test site, in that the first stimulus of a series of stimuli forming an examination is presented at any test site with an intensity value;

correcting for this test site and the test sites located within its predetermined circle, the stimulus intensity value according to a patient response towards the threshold value of perception; and recording the patient responses as corrected stimulus intensity values, and in that a second stimulus and following stimuli which are presented at other test sites in any sequence have the initial value or corrected stimulus intensity value recorded for the respective test site.

2. Method according to claim 1, further comprising a step of dividing the test sites into n groups, and in that no test site of one group is located within the circle of a test site of the same group, in that one stimulus is applied in each case firstly to the test sites of the first group, then to those of the second group, and further groups, and finally to those of the nth group.

3. Method according to claim 2, wherein the stimulus intensity value provided for each test site is half an age-corrected standard value of a subject known for this test site.

4. Method according to claim 3, further comprising steps of changing the value of a stimulus, wherein the initial value for each test site of the first group is increased or reduced after the measurement in accordance with the patient response, seen or not seen, by a first constant to give a corrected stimulus intensity value, which constant corresponds as a rough approximation to half the average of the age-corrected standard values of all test sites;

adapting initial values of stimuli at the test sites of the other groups by interpolation and/or extrapolation to the corrected stimulus intensity values of the first group, in that, after the examination, the stimulus intensity values of the second group, corrected in this manner, are increased or reduced by a second constant—in accordance with the patient response— which second constant is smaller than the first constant; and correcting the already corrected stimulus intensity values of the non-examined test sites again by interpolation and/or extrapolation, and in that the same procedure is applied in the following groups, the third constant being smaller than the second and the fourth constant being smaller than the third.

5. Apparatus for testing visual function of the human eye, comprising:

means which impose a predetermined direction of view during an examination;

means to present stimuli at predetermined test sites, determined in respect of the position, within a surrounding area of the direction of view;

a computer which controls the means for applying the stimuli both in respect of the position and in respect of the strength;

a memory assigned to the computer which, on the one hand, stores a stimulus intensity value for each test site and which, on the other hand, is assigned a response device for signalling the patient response;

wherein the computer is programmed to apply a stimulus only once at each test site, in that the computer is programmed further to provide that an initial value for the stimulus is stipulated and recorded for each test site, wherein the first stimulus of a series of stimuli forming an examination is presented at any test site with said intensity value, the computer performing steps of:

correcting for this test site, and the test sites located within its predetermined circle, the stimulus intensity value according to the patient response towards the threshold value of perception; and recording these patient responses as corrected stimulus intensity values, and in that a second stimulus and following stimuli which are presented at other test sites in any sequence have the initial value or corrected stimulus intensity value recorded for the respective test site.

6. A method for evaluating visual function of an eye, comprising steps of:

establishing a plurality of grids over a test field wherein grid points of any one of said grids are spaced between grid points of other ones of said plurality of grids;

determining values of stimuli detection threshold at grid points of said grids, said determining comprising steps of:

applying sets of optical stimuli at respective ones of the grid points of a first one of said grids at successive instants of time for observation by said eye;

at each of said grid points of said first grid, in an individual one of said sets of optical stimuli, incrementing the intensity of the optical stimuli via a first sequence of increments of decreasing magnitude, wherein any one of said increments may be positive or negative, to establish a threshold of detection of intensity of optical stimulus by said eye at each grid point of said first grid; and interpolating values of thresholds of said first grid to obtain interpolated values of threshold for grid points of other grids of said plurality of grids;

wherein the method further comprises steps of repeating said threshold determining step for a second grid and successively for further grids of said plurality of grids; and in each of a succession of repetitions of said threshold determining step, adjusting the sequence of increments based on values of threshold established by prior steps of the interpolating for reduction of the number of stimuli in the sets of the stimuli at the respective grid points.

7. Apparatus for evaluating visual function of the eye, comprising:

a display presenting results of an evaluation;

perimeter means for presenting a succession of visual stimulations at each of a plurality of locations;

means for signaling a response of a person upon detection of a stimulus by the person's eye;

computer means for activating the perimeter means to produce stimuli of a determined magnitude, the computer means receiving a signal from the signaling means designating the occurrence of a detection by the person, the computer means outputting results of the evaluation to the display; and wherein the computer is operative to establish values of stimulation and to interpolate among values of detected stimuli in accordance with a sequence of method steps of:

establishing a plurality of grids over a test field wherein grid points of any one of said grids are spaced between grid points of other ones of said plurality of grids;

determining values of stimuli detection threshold at grid points of said grids, said determining comprising steps of:

applying sets of optical stimuli at respective ones of the grid points of a first one of said grids at successive instants of time for observation by said eye;

at each of said grid points of said first grid, in an individual one of said sets of optical stimuli, incrementing the intensity of the optical stimuli via a first sequence of increments of decreasing magnitude, wherein any one of said increments may be positive or negative, to establish a threshold of detection of intensity of optical stimulus by said eye at each grid point of said first grid; and interpolating values of thresholds of said first grid to obtain interpolated values of threshold for grid points of other grids of said plurality of grids;

wherein the method further comprises steps of repeating said threshold determining step for a second grid and successively for further grids of said plurality of grids; and in each of a succession of repetitions of said threshold determining step, adjusting the sequence of increments based on values of threshold established by prior steps of the interpolating for reduction of the number of stimuli in the sets of the stimuli at the respective grid points.

* * * * *